United States Patent
Frigstad et al.

(10) Patent No.: US 10,543,074 B2
(45) Date of Patent: Jan. 28, 2020

(54) PASSIVE ARTIFICIAL SPHINCTER

(71) Applicant: AMS Research, LLC, Minnetonka, MN (US)

(72) Inventors: John R. Frigstad, St. Anthony, MN (US); Amanda J. Heys, Eden Prairie, MN (US); William A. Sturos, Elk River, MN (US); Daniel R. Parks, Big Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/395,920

(22) PCT Filed: Mar. 1, 2013

(86) PCT No.: PCT/US2013/028547
§ 371 (c)(1),
(2) Date: Oct. 21, 2014

(87) PCT Pub. No.: WO2013/165541
PCT Pub. Date: Nov. 7, 2013

(65) Prior Publication Data
US 2015/0105859 A1 Apr. 16, 2015

Related U.S. Application Data

(60) Provisional application No. 61/641,436, filed on May 2, 2012.

(51) Int. Cl.
*A61F 2/08* (2006.01)
*A61F 2/02* (2006.01)
(Continued)

(52) U.S. Cl.
CPC ............ *A61F 2/08* (2013.01); *A61B 17/1214* (2013.01); *A61F 2/0036* (2013.01);
(Continued)

(58) Field of Classification Search
CPC ................... A61F 2/004; A61F 2/0036; A61F 2002/0894; A61F 2220/0025; A61F 2/0018; A61B 17/1214; A61B 2018/00553
(Continued)

(56) References Cited

U.S. PATENT DOCUMENTS

2004/0200236 A1* 10/2004 Emberson .............. A44C 15/00
63/23
2004/0267291 A1* 12/2004 Byrum .................... A61F 5/005
606/157
(Continued)

FOREIGN PATENT DOCUMENTS

WO 2013165541 A1 11/2013

OTHER PUBLICATIONS

International Search Report and Written opinion of PCT/US2013/028547, dated May 3, 2013.

*Primary Examiner* — Dinah Baria
(74) *Attorney, Agent, or Firm* — Brake Hughes Bellermann LLP

(57) ABSTRACT

A passive artificial sphincter includes a tension member, an outer sleeve, and a connecter. The tension member has first and second ends. The outer sleeve contains the tension member and is formed of a biocompatible material. The connecter is configured to couple the first and second ends together to form an artificial sphincter ring. The artificial sphincter ring is configured for implantation around the lumen to provide passive constriction of the lumen.
In a method, an artificial sphincter comprising a tension member contained within an outer sleeve is positioned around a lumen of a patient. The lumen is constricted responsive to the tension in the tension member. The passage
(Continued)

of material through the lumen and past the artificial sphincter ring is resisted responsive to the constriction of the lumen.

11 Claims, 5 Drawing Sheets

(51) Int. Cl.
  *A61F 2/00* (2006.01)
  *A61B 17/12* (2006.01)
  *A61B 18/00* (2006.01)

(52) U.S. Cl.
  CPC ............... *A61B 2018/00553* (2013.01); *A61F 2002/0894* (2013.01); *A61F 2210/0014* (2013.01); *A61F 2220/0025* (2013.01); *A61F 2220/0033* (2013.01)

(58) Field of Classification Search
  USPC ............... 623/2.36, 14.13, 23.67; 600/30, 31
  See application file for complete search history.

(56) References Cited

U.S. PATENT DOCUMENTS

| | | | |
|---|---|---|---|
| 2005/0125075 A1* | 6/2005 | Meade | A61B 17/0401 |
| | | | 623/23.64 |
| 2007/0135913 A1* | 6/2007 | Moaddeb | A61F 2/2445 |
| | | | 623/2.37 |
| 2009/0118749 A1* | 5/2009 | Shalon | A61F 5/0079 |
| | | | 606/157 |
| 2009/0240340 A1 | 9/2009 | Levine et al. | |
| 2010/0076573 A1 | 3/2010 | Kugler et al. | |
| 2011/0098731 A1* | 4/2011 | Whitbrook | A61F 2/0018 |
| | | | 606/151 |
| 2013/0053874 A1* | 2/2013 | Ekvall | A61N 2/06 |
| | | | 606/157 |

* cited by examiner

PASSIVE ARTIFICIAL SPHINCTER

CROSS-REFERENCE TO RELATED APPLICATION

This Application is a Section 371 National Stage Application of International Application No. PCT/US2013/028547 filed Mar. 1, 2013 and published as WO/2013165541 A1 in English, which claims the benefit of U.S. Provisional Application Ser. No. 61/641,436, filed May 2, 2012 under 35 U.S.C § 119(e). The contents of each of the above-identified applications are herby incorporated by reference in their entirety.

BACKGROUND

Artificial sphincters are devices that are implanted in patients to assist in occluding lumens of the patient to control a flow of material through the lumen. For instance, artificial sphincters have been implanted around the urethra to treat urinary incontinence.

Conventional artificial sphincters are "active" artificial sphincters that operate to provide a desired constrictive force to occlude a lumen of a patient responsive to input from the patient. Typical active artificial sphincters comprise a cuff, a reservoir and a pump. The cuff is wrapped around the lumen, the reservoir is implanted in an abdominal cavity, and the pump is implanted at a location that may be actuated by the patient, such as in the scrotum of the patient. Tubing connects the reservoir, pump and cuff. The reservoir pressurizes fluid in the system and maintains the cuff in an inflated state, in which a constrictive force is applied to the lumen to occlude the lumen. Actuation of the pump drives fluid out of the cuff and back into the reservoir to deflate the cuff. This removes the constrictive force on the lumen and allows the passage of material through the lumen and past the cuff.

The implantation of such an active artificial sphincter can be quite invasive due to the number and volume of the components. Additionally, the control of the artificial sphincter requires input from the patient, which may be difficult for some patients.

BRIEF DESCRIPTION OF THE DRAWINGS

FIG. 3 is an isometric view of a cuff member section formed in accordance with embodiments of the invention.

FIG. 4 is an isometric view of an artificial sphincter formed in accordance with embodiments of the invention.

SUMMARY

Figure 1:
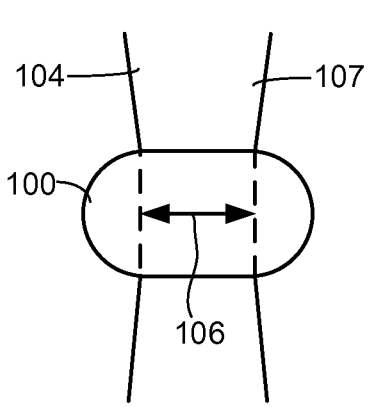
FIGS. 1 and 2 are simplified drawings respectively illustrating an artificial sphincter formed in accordance with embodiments of the invention in a closed and open position.

Embodiments of the invention are directed to a passive artificial sphincter and methods of constricting a lumen using embodiments of the passive artificial sphincter. In some embodiments, the artificial sphincter (100) comprises a tension member (110), an outer sleeve (112), and a connecter (126). The tension member has first and second ends (124). The outer sleeve contains the tension member and is formed of a biocompatible material. The connecter is configured to couple the first and second ends together to form an artificial sphincter ring (128). The artificial sphincter ring is configured for implantation around the lumen (104) to provide passive constriction of the lumen.

In some embodiments, the tension member comprises a plurality of short tension members (114) each having one end (130) coupled to an end (130) of another short tension member.

In some embodiments, the sleeve comprises of material selected from the group consisting of polyethylene, polypropylene, and polyvinyl acetate. In some embodiments, the outer sleeve is tubular.

In some embodiments, the tension member comprises a tension spring (120) having a longitudinal axis (116). The tension spring resists expansion along the longitudinal axis. In some embodiments, the tension spring comprises Nitinol (NiTi) and/or steel. In some embodiments, the tension spring comprises a coil spring.

In some embodiments, the tension spring comprises a plurality of struts (142) each having an end (144) joined to an end of another strut at flexible joints (146). In some embodiments, the tension spring comprises a plurality of expansion members (150) each attached to one of the struts. The expansion members expand a thickness of the tension spring and decrease the interior diameter (106) of the artificial sphincter ring.

In some embodiments, the connector comprises a first connecter (126A) attached to the first end of the tension member, and a second connecter (126B) attached to the second end of the tension member. First and second connectors are configured to couple the first and second ends of the tension member together to form the artificial sphincter ring. In some embodiments, at least one of the first and second connectors comprises a magnet (136). In some embodiments, the first connector comprises a male connector (132), and the second connector comprises a female connector (134) that receives the male connector to couple the first and second ends of the tension member together.

In some embodiments of the method, an artificial sphincter (100) comprising a tension member (110) contained within an outer sleeve (112) is positioned (160) around a lumen (104) of the patient. First and second ends (124) of the artificial sphincter are coupled together (172) to form an artificial sphincter ring (128) around the lumen. The lumen is constricted (174) responsive to the tension in the tension member. The passage of material through the lumen and past the artificial sphincter ring is resisted (176) responsive to the constriction of the lumen.

In some embodiments of the method, the artificial sphincter ring is expanded in response to internal pressure within the lumen. Material is allowed to pass through the lumen and past the artificial sphincter ring, responsive to the expansion of the artificial sphincter ring.

In some embodiments, the first and second ends of the artificial sphincter are coupled together by joining a first connector (126A) attached to the first end to a second connecter (126B) attached to the second end. In some embodiments, the first and second connectors comprise a magnet (136), a male connecter (132), or a female connector (134).

In some embodiments of the method, the artificial sphincter is positioned around the lumen of the patient by supporting the artificial sphincter in a corkscrew-shape using a deployment member (162). In some embodiments, the artificial sphincter (100) is supported by a corkscrew-shaped needle (164). The deployment member is then rotated around the lumen in a first direction (168). The artificial sphincter is then deployed from the deployment member to place the artificial sphincter around the lumen. In some embodiments, the deployment of the artificial sphincter from the deployment member involves rotating the deployment member around the lumen in a second direction that is opposite the first direction relative to the artificial sphincter. The deployment member is then removed from the patient to complete the positioning of the artificial sphincter around the lumen. The implantation of the artificial sphincter around the lumen is completed following the coupling of the ends of the artificial sphincter.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Embodiments of the invention are directed to an artificial sphincter that is configured to passively apply a constrictive force to a lumen of a patient without a control input from the patient, as required by active artificial sphincters. Additionally, embodiments of the artificial sphincter require fewer components to be installed in the patient thereby reducing the invasiveness of the implantation, the complexity of the installation, and the likelihood of component failure. Some applications of the passive artificial sphincter, such as to prevent fecal incontinence, allow the patient to control the artificial sphincter in a natural manner, making the implantation highly inconspicuous, as compared to conventional active artificial sphincters.

Embodiments of the invention are described more fully hereinafter with reference to the accompanying drawings.

The various embodiments of the invention may, however, be embodied in many different forms and should not be construed as limited to the embodiments set forth herein. Rather, these embodiments are provided so that this disclosure will be thorough and complete, and will fully convey the scope of the invention to those skilled in the art. Elements that are identified using the same or similar reference characters refer to the same or similar elements.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will be understood that when an element is referred to as being "connected" or "coupled" to another element, it can be directly connected or coupled to the other element or intervening elements may be present. In contrast, if an element is referred to as being "directly connected" or "directly coupled" to another element, there are no intervening elements present. Embodiments of the invention include both interpretations unless stated otherwise.

It will be understood that, although the terms first, second, etc. may be used herein to describe various elements, these elements should not be limited by these terms. These terms are only used to distinguish one element from another. Thus, a first element could be termed a second element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
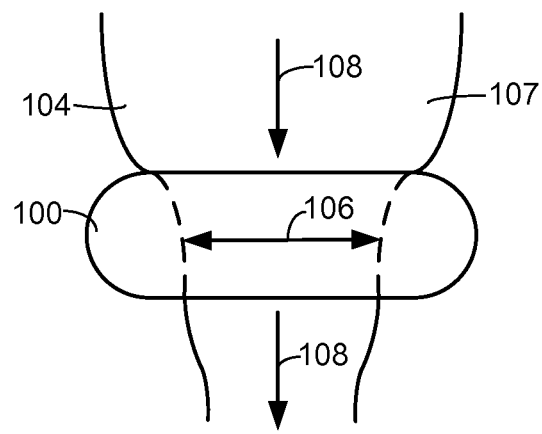

FIGS. 1 and 2 are simplified diagrams of a passive artificial sphincter 100 in accordance with embodiments of the invention implanted around a lumen (i.e., a passageway) 104 of a patient. Exemplary embodiments of the lumen 104 include the urethra, the anal canal, the esophagus, a lumen of an ostomy, or other lumen of a patient. The artificial sphincter 100 provides circumferential occlusion of the lumen 104. This may be accomplished by implanting the artificial sphincter 100 directly around the lumen 104, such as upstream or downstream of a sphincter muscle (e.g., anal sphincter) controlling flow through the lumen 104. Alternatively, the artificial sphincter 100 may be implanted around a sphincter muscle corresponding to the lumen 104 to reinforce the sphincter muscle and assist in occluding the lumen. Accordingly, embodiments of positioning, placing or implanting the artificial sphincter 100 around a lumen 104 of the patient include the implantation of the artificial sphincter 100 around a sphincter muscle corresponding to the lumen 104.

In some embodiments, the constrictive force applied by the artificial sphincter 100 to the lumen 104 is a substantially uniform force applied around the circumference of the lumen 104 that is continuously applied by the artificial sphincter 100 to the lumen 104. In some embodiments, the constrictive force closes the lumen 104, or assists another sphincter to close the lumen 104, to prevent or reduce the passage of material through the lumen 104, and past the artificial sphincter 100, as shown in FIG. 1. That is, the constrictive force of the artificial sphincter 100 results in the internal diameter 106 of the artificial sphincter 100 and the outer diameter of the lumen 104 to reach a closed state where the lumen 104 is closed or substantially closed to the passage of material through the lumen 104, and past the artificial sphincter 100, as shown in FIG. 1.

In some embodiments, the artificial sphincter 100 may be transitioned to an open state (FIG. 2), in which material may pass through the lumen 104 and past the artificial sphincter 100. In some embodiments, the artificial sphincter 100 transitions from the closed state to the open state in response to sustained pressure within the lumen 104 on the upstream side 107 of the artificial sphincter 100 relative to the normal flow of material through the lumen represented by arrows 108. This pressure counteracts the constrictive force applied by the artificial sphincter 100 and causes the internal diameter 106 of the artificial sphincter 100 to expand radially, as shown in FIG. 2. This expansion of the artificial sphincter 100 allows material to flow through the lumen 104 and past the artificial sphincter 100, as indicated by arrows 108 in FIG. 2.

For instance, when the artificial sphincter 100 is implanted around the anal canal of the patient, the artificial sphincter 100 constricts the anal canal, or assists the anal sphincter in constricting the anal canal, under normal abdominal conditions to prevent fecal incontinence, as illustrated in FIG. 1. When the patient wishes to have a bowel movement, the patient increases abdominal pressure in a natural manner to increase the pressure within the lumen 104 on the upstream side 107 of the artificial sphincter 100, which causes the artificial sphincter 100 to radially expand and allow the bowel movement to occur, as shown in FIG. 2.

Figure 3:
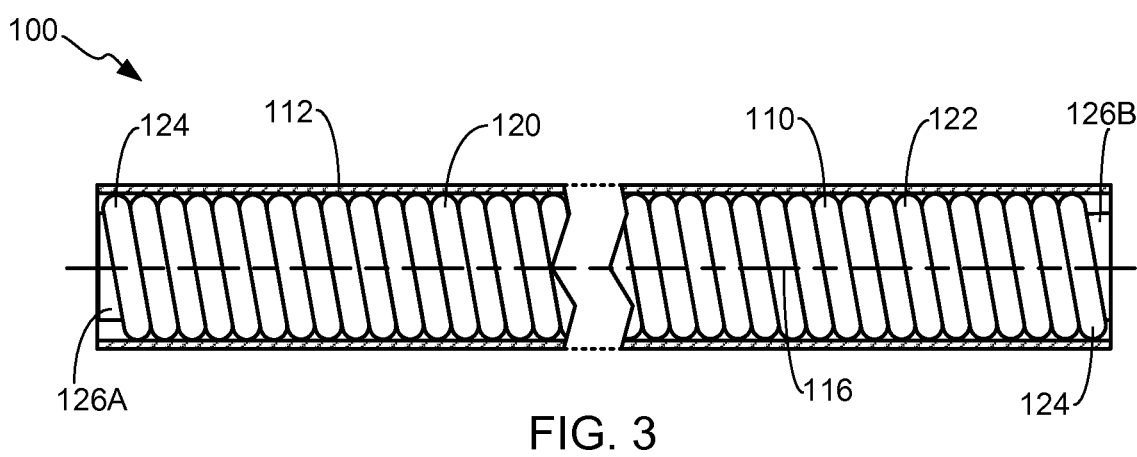
FIGS. 3 and 4 are side views of an artificial sphincter in accordance with embodiments of the invention with portions shown in cross-section.

In some embodiments, the artificial sphincter 100 comprises a tension member 110 contained within a biocompatible outer sleeve 112, as illustrated in FIG. 3, which is a side view of the artificial sphincter 100 with the outer sleeve 112 shown in cross-section. In some embodiments, the tension member 110 is formed of multiple short tension members 114. The use of multiple short tension members 114 to form the tension member 110 allows for customized lengths of the tension member 110 through the use of more or fewer tension members 114, and/or different sized tension members 114. Additionally, different short tension members 114 can be used to provide different constrictive forces when the artificial sphincter 100 is implanted around a lumen 104. Other properties of the artificial sphincter 100 may also be adjusted through the selection of the short tension members 114.

Figure 4:
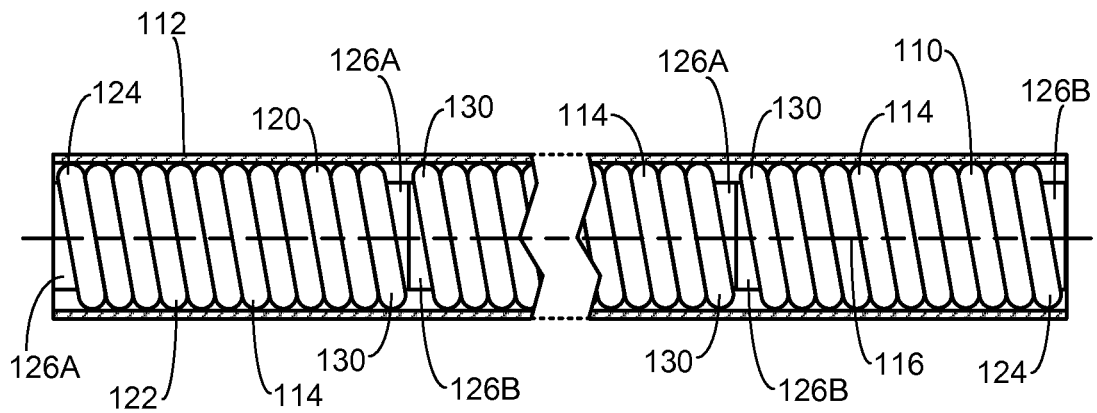
Figure 5:
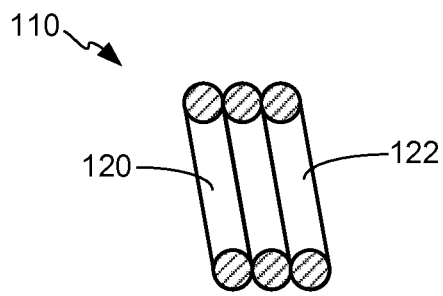
FIGS. 5 and 6 are cross-sectional views of a tension coil in accordance with embodiments of the invention.
Figure 6:
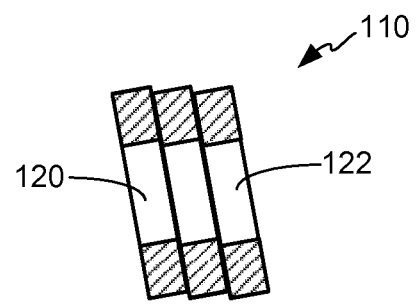

In some embodiments, the tension member 110, as well as the short tension members 114, comprise a tension spring 120, which is configured to resist expansion or stretching along a longitudinal axis 116 (FIGS. 3 and 4). Exemplary materials that may be used to form the tension spring 120 include Nitinol (NiTi), steel, or other suitable material. In some embodiments, the tension spring 120 is in the form of a coil spring, and the radial constrictive force exerted by the tension spring 120 against a lumen 124 is controlled by setting the wind, pitch, and shape of the coils forming the tension spring 120. In some embodiments, the tension spring 120 comprises a wire 122 having a circular cross-sectional shape, as shown in FIG. 5. In some embodiments, the wire 122 of the tension spring 120 has a square or rectangular cross-sectional shape, as shown in FIG. 6. Other configurations for the tension spring 120 and the wire 122 may also be used.

In some embodiments, the sleeve 112 is formed of a flexible material that may expand and contract along with the tension member 110. In some embodiments, the sleeve 112 is tubular in shape. In some embodiments, the material forming the sleeve 112 has a low adherence to the exterior surface of the lumen 104 to allow the sleeve 112 to slide relative to the lumen 104 as it constricts the lumen 104, or expands to open the lumen 104. Exemplary materials suitable for forming the sleeve 112 include polyethylene, polypropylene, polyvinyl acetate, or other suitable material.

Figure 7:
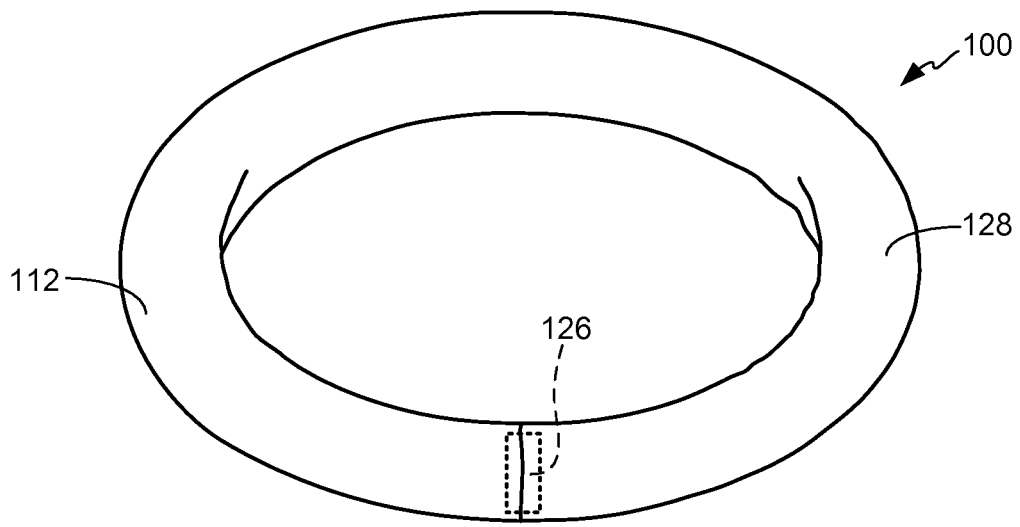
FIG. 7 is an isometric view of an artificial sphincter ring in accordance with embodiments of the invention.

In some embodiments, ends 124 (FIGS. 3 and 4) of the artificial sphincter 100 or the tension member 110 are coupled together using a connector, generally referred to as 126, to form an artificial sphincter ring 128, such as that illustrated in FIG. 7. The artificial sphincter ring 128 provides the desired occlusion of a lumen 104. Connectors 126 may also be used to join ends 130 (FIG. 4) of the short tension members 114 together to form the tension member 110.

In some embodiments, the connectors 126 comprise cooperating connectors 126A and 126B. In some embodiments, the connector 126A is attached to one of the ends 124 of the tension member 110, and the connector 126B is attached to the other end 124, as shown in FIG. 3. In some embodiments, the connectors 126A and 126B may be attached to opposing ends 130 of the short tension members 114. This allows the connector 126A at the end 130 of one short tension member 114 to connect to the connector 126B at the end 130 of an adjoining short tension member 114, as shown in FIG. 4.

Figures 8, 9, 10:
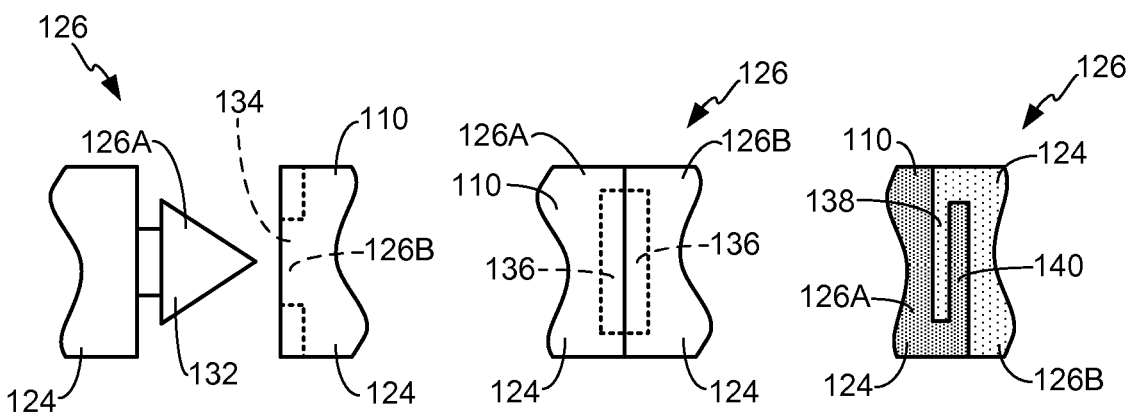
FIGS. 8 and 9 are simplified side views of cooperating connectors in accordance with embodiments of the invention on ends of an artificial sphincter.
FIG. 10 is a simplified cross-sectional view of cooperating connectors in accordance with embodiments of the invention on ends of an artificial sphincter.

The connectors 126A and 126B can take on many different forms. FIGS. 8-10 are simplified side views of exemplary connectors 120 in accordance with embodiments of the invention. In some embodiments, the connector 126A includes a male connector 132, such as a protrusion, and the connector 126B includes a female connector 134 that receives the male connector 132, such as a socket, to couple the ends 124 of the tension member 110 together, as shown in FIG. 8, or to couple the ends 130 of the short tension members 114 together. In some embodiments, the cooperating male and female connectors 132 and 134 snap together.

In some embodiments, the connectors 126A and 126B each include a magnet 136, as illustrated in FIG. 9. The adjoining faces of the magnets 136 have opposing polarities to magnetically adhere the connector 126A to the connector 126B. In some embodiments, the connectors 126A and 126B include cooperating structures, such as a protrusion and a socket, to ensure proper attachment and orientation.

In accordance with another embodiment, the connectors 126A and 126B include cooperating slide-lock connectors 138 and 140, respectively, as shown in FIG. 10. The slide-lock connectors 138 and 140 each include a protrusion that is received within a socket of the other slide-lock connector to join the connectors 126A and 126B together.

Figure 11:
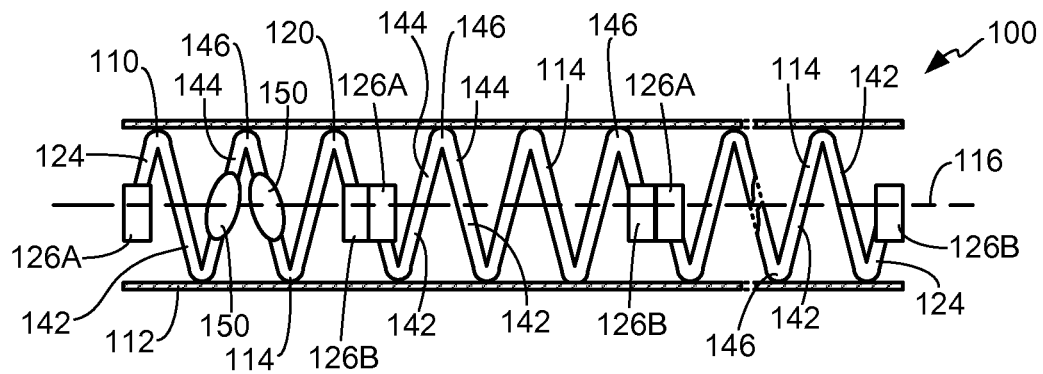
FIG. 11 is a side view of an artificial sphincter in accordance with embodiments of the invention with portions shown in cross-section.
Figure 12:
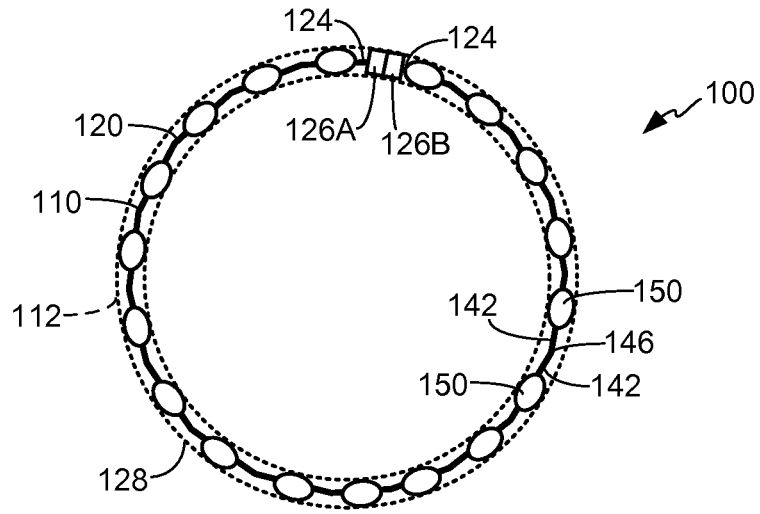
FIG. 12 is a top view of the artificial sphincter of FIG. 11 formed into an artificial sphincter ring in accordance with embodiments of the invention.

FIG. 11 is a side view of an artificial sphincter 100 in accordance with embodiments of the invention. FIG. 12 is a top view of the artificial sphincter 100 of FIG. 11 formed into an artificial sphincter ring 128 using the connector 126, in accordance with embodiments of the invention.

In some embodiments, the tension member 110 comprises a tension spring 120 that includes a plurality of struts 142. Opposing ends 144 of the struts 142 are joined together at flexible joints 146 that resist expansion of the struts along a longitudinal axis 116 (FIG. 11). The struts 142 and joints 146 may be formed of steel, Nitinol (NiTi) or other suitable material.

In some embodiments, the struts 142 are contained within an outer sleeve 112 that is preferably formed of a biocompatible material such as that used to form the sleeve 112, as discussed above. In some embodiments the sleeve 112 wraps around the tension spring 120 covering areas between the struts 142.

Figure 13:
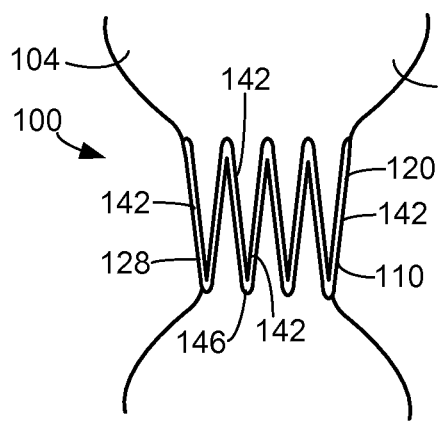
FIGS. 13 and 14 illustrate embodiments of the artificial sphincter of FIGS. 11 and 12 implanted around an exemplary lumen in closed and open positions, respectively.
Figure 14:
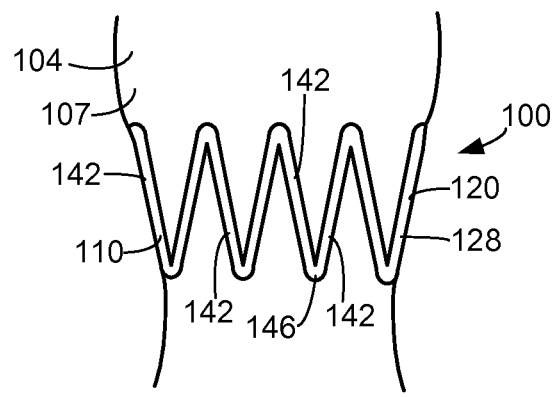

FIGS. 13 and 14 are simplified side views of the artificial sphincter 100 of FIGS. 11 and 12 implanted around an exemplary lumen in closed and open positions, respectively. The sleeve 112 is not shown in FIGS. 13 and 14 in order to simplify the illustrations. When the artificial sphincter 100 is in the closed position, the struts 142 are pulled closely together to constrict the lumen 104 and prevent or inhibit the passage of material through the lumen and past the artificial sphincter 100, as discussed above. The patient may generate pressure within the lumen 104 that causes the joints 146 to bend and expand the tension spring 120, as shown in FIG. 14. This expansion of the artificial sphincter 100 allows material to pass through the lumen 104 and past the artificial sphincter 100, as discussed above.

In some embodiments, the tension spring 120 includes a plurality of expansion members 150, shown in FIGS. 11 and 12, that operate to increase a thickness of the tension spring 120, and decrease the interior diameter 108 of the artificial sphincter ring 128. In some embodiments, the expansion members 150 are each attached to one of the struts 142. The expansion members 150 include portions that extend radially inward from the struts 142 to reduce the internal diameter of the artificial sphincter 100. The expansion members 150 increase the constrictive force that is applied to the lumen 104 by the artificial sphincter 100 due to the radial displacement of the tension spring 120 from the lumen 104 by the expansion members 150.

In some embodiments, ends 124 of the tension spring 120 are connected together using one or more of the embodiments of the connector 126 described above, such as cooperating connectors 126A and 126B, as illustrated in FIG. 12. In some embodiments, the tension spring 120 comprising the struts 142 are divided into short tension members 114 that join together using connectors 126A and 126B to form the tension member 110, as shown in FIG. 11. In some embodiments, the tension member 110 is formed of a single tension spring 120, as shown in FIG. 12.

Figure 15:
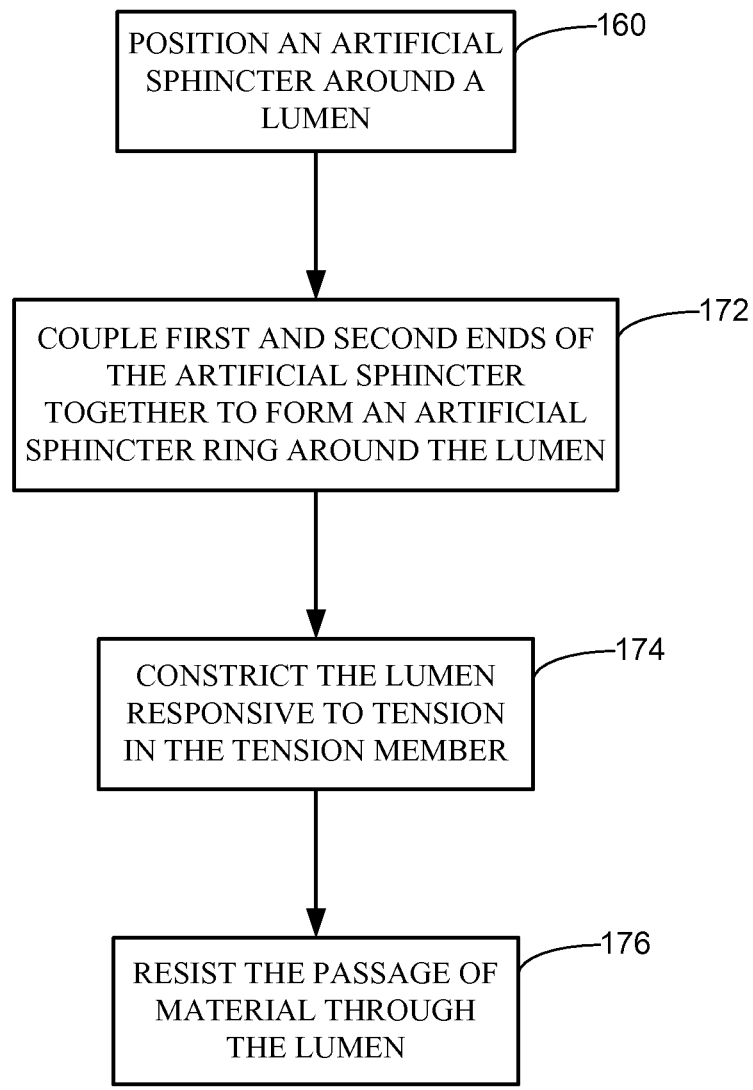
FIG. 15 is a flowchart illustrating a method of passively constricting a lumen of a patient in accordance with embodiments of the invention.

Additional embodiments are directed to methods of passively constricting a lumen of a patient using the artificial sphincter 100, formed in accordance with one or more embodiments described above. FIG. 15 is a flowchart illustrating a method of passively constricting a lumen of a patient in accordance with embodiments of the invention. At 160, an artificial sphincter 100 comprising a tension member 110 contained within an outer sleeve 112, is positioned around a lumen 104. The positioning step 160 requires an incision in the patient to position the artificial sphincter 100 around the lumen 104. Exemplary embodiments of a lumen 104 include the urethra, the anal canal, the esophagus, a lumen of an ostomy of the patient, or other lumen.

In some embodiments, one of the ends 124 of the artificial sphincter 100 may have a blunt tip that may assist in the implantation of the artificial sphincter around the lumen 104 during the positioning step 160. The blunt tip may be formed of polyurethane, rubber, ethylene-vinyl acetate, polyester, polypropylene, or other similar material. In some embodiments, the blunt tip is attached to the end 124 of the tension member 110 using suitable cooperating connectors, such as those described above with regard to the connecter 126.

Figure 16:
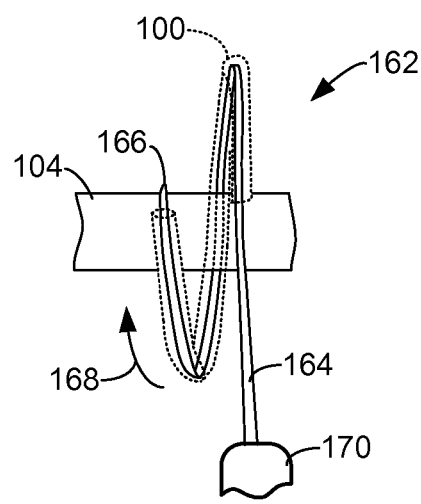
FIGS. 16 and 17 respectively are simplified side and front views of a technique of positioning an artificial sphincter around a lumen in accordance with embodiments of the invention.
Figure 17:
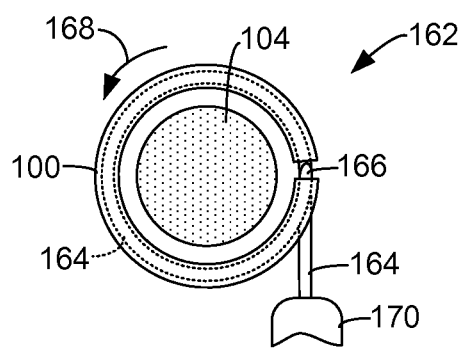
Figure 18:
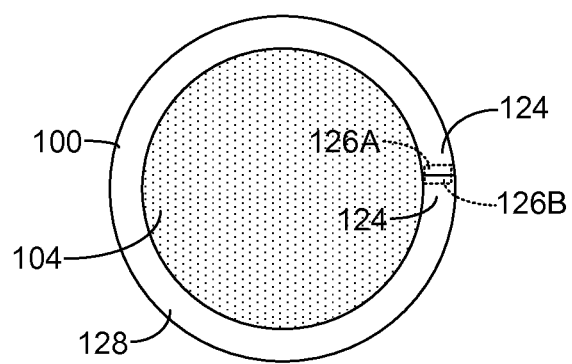
FIG. 18 is a simplified front view of an artificial sphincter implanted around a lumen of a patient.

In some embodiments of step 160, the artificial sphincter 100 is supported in a corkscrew-shape using a deployment member 162, as illustrated in FIGS. 16-18. Some embodiments of the deployment member 162 include a corkscrew-shaped needle 164, as illustrated in the simplified side view of FIG. 16, in which the artificial sphincter 100 is illustrated in phantom lines. In some embodiments, the artificial sphincter 100 (i.e., tension member 110 and sleeve 112) is slid over, or attached to, a distal end 166 of the needle 164. One alternative to attaching the artificial sphincter 100 to the distal end 166 of the needle 164 is to use an introducer-type needle as the needle 164, which allows the artificial sphincter 100 to be received within the cork screw-shaped distal end 166.

In some embodiments, the distal end 166 of the needle 164 is brought in close proximity to the lumen 104 and rotated about the lumen 104 in the direction 168 until the needle 164 and the supported artificial sphincter 100 surround the lumen 104, as shown in FIG. 16 and the simplified front view provided in FIG. 17. In some embodiments, the deployment member 162 includes a handle 170 that can be used to assist in the rotation of the needle 164 about the lumen 104.

Once the artificial sphincter 100 is positioned around the lumen 104, the artificial sphincter 100 is deployed from the deployment member 162 to place the artificial sphincter 100 around the lumen 104, as illustrated in FIG. 18. In some embodiments, the deployment of the artificial sphincter 100 involves rotating the needle 164 about the lumen 104 relative to the artificial sphincter 100 in the opposite direction from 168. This may involve holding the artificial sphincter 100 in position as the needle 164 is rotated when the artificial sphincter 100 is supported on the exterior of the needle 164. Alternatively, when the needle 164 is in the form of an inducer needle, the deployment of the artificial sphincter 100 around the lumen 104 involves discharging the artificial sphincter 100 from the introducer needle 164 as the needle 164 is rotated about the lumen 104 in the direction opposite 168. Finally, the deployment member 162 is removed from the patient to complete the positioning of the artificial sphincter 100 around the lumen 104.

At 172 of the method, first and second ends 124 of the artificial sphincter are coupled together to form an artificial sphincter ring 128 around the lumen, as shown in FIG. 18. In some embodiments, step 172 involves stretching the tension member 110 of the artificial sphincter 100, which places the tension member 110 in tension around the lumen.

The connection of the ends 124 may be accomplished using a connector 126 formed in accordance with one or more embodiments described above. In some embodiments of step 172, a first connecter 126A attached to one of the ends 124 is joined to a second connecter 126B attached to the other end 124 of the artificial sphincter, as shown in FIG. 18. In some embodiments, the connecters 126A and 126B comprise a magnet, a male connecter, a female connecter, or other suitable connector, as discussed above.

At 174, the lumen 104 is constricted in response to the tension in the tension member 110, as illustrated in FIGS. 1 and 13. At 176, the passage of material through the lumen 104 and past the artificial sphincter ring 128 is resisted or prevented in response to the restriction of the lumen 104 in step 174.

In some embodiments, the artificial sphincter ring 128 may be expanded in response to internal pressure within the lumen, as illustrated in FIGS. 2 and 14. This allows for the passage of material through the lumen and past the artificial sphincter ring 128.

Although the present invention has been described with reference to preferred embodiments, workers skilled in the art will recognize that changes may be made in form and detail without departing from the spirit and scope of the invention.

What is claimed is:

1. A passive artificial sphincter comprising:
a tension member including a tension spring, the tension spring having a first member having a plurality of struts and a second member having a plurality of struts, the tension spring resist expansion to provide a constrictive force to a lumen of a patient, the first member having a first length and the second member having a second length being different than the first length, a first connector being connected to one end of the first member and a second connector being connected to the other end of the first member, a third connector being connected to one end of the second member and a fourth connector being connected to the other end of the second member, the first connector being configured to be removably coupled to the third connector;
an outer sleeve containing the tension spring, the outer sleeve being formed of a biocompatible material; and
a plurality of expansion members, each of the plurality of expansion members being coupled to one of the plurality of struts of the first member and include a portion that extends radially inward from the one of the plurality of struts of the first member; wherein the plurality of expansion members increase constrictive force of the passive artificial sphincter.

2. The artificial sphincter according to claim 1, wherein the outer sleeve comprises a material selected from the group consisting of polyethylene, polypropylene, and polyvinyl acetate.

3. The artificial sphincter according to claim 1, wherein the outer sleeve wraps around the tension spring including areas disposed between the plurality of struts of the first member and the second member.

4. The artificial sphincter according to claim 1, wherein a number of the plurality of struts of the first member is less than a number of the plurality of struts of the second member.

5. The artificial sphincter according to claim 1, wherein the tension spring includes materials selected from the group consisting of Nitinol (NiTi) and steel.

6. The artificial sphincter according to claim 1, wherein the plurality of expansion members are configured to reduce an interior diameter of a ring formed by the tension spring.

7. The artificial sphincter of claim 1, wherein the plurality of expansion members include a first expansion member and a second expansion member, wherein the first expansion member is coupled to one of the plurality of struts of the first member and the second expansion member is coupled to another one of the plurality of struts of the first member.

8. A passive artificial sphincter comprising:
a tension member including a tension spring, the tension spring having a first member having a plurality of struts and a second member having a plurality of struts, the tension spring resist expansion to provide a constrictive force to a lumen of a patient, the first member having a first length and the second member having a second length being different than the first length, a first connector being connected to one end of the first member and a second connector being connected to the other end of the first member, a third connector being connected to one end of the second member and a fourth connector being connected to the other end of the second member, the first connector being configured to be removably coupled to the third connector to form a ring;
an outer sleeve containing the tension spring, the outer sleeve formed of a biocompatible material; and
a plurality of expansion members, each of the plurality of expansion members being coupled to one of the plurality of struts of the first member and include a portion that extends radially inward from the one of the plurality of struts of the first member wherein the plurality of expansion members increase constrictive force of the passive artificial sphincter, and,
wherein the ring is configured for implantation within a body of a patient, the ring being configured to engage a deployment member, the deployment member includes a cork-screw shaped needle.

9. The artificial sphincter according to claim 8, wherein the plurality of expansion members are configured to reduce an internal diameter of the ring.

10. The artificial sphincter of claim 8, wherein the artificial sphincter has a closed position and an open position, wherein when the artificial sphincter is in the closed position, the plurality of struts of the first member and the second member are pulled closer together to constrict the urethra.

11. The artificial sphincter of claim 8, wherein a number of the plurality of struts of the first member is less than a number of the plurality of struts of the second member.

* * * * *